United States Patent [19]

Fischer

[11] Patent Number: 5,759,037

[45] Date of Patent: Jun. 2, 1998

[54] METHODS FOR MANUFACTURING DENTAL TRAYS HAVING THIN WALLS FOR INCREASED COMFORT

[76] Inventor: Dan E. Fischer. 10444 S. Dimple Dell Rd., Sandy, Utah 84093

[21] Appl. No.: 721,008

[22] Filed: Sep. 26, 1996

Related U.S. Application Data

[62] Division of Ser. No. 378,315, Jan. 25, 1995, which is a continuation of Ser. No. 99,247, Jul. 28, 1993, abandoned, which is a continuation of Ser. No. 985,700, Dec. 2, 1992, abandoned, which is a continuation of Ser. No. 718,210, Jun. 20, 1991, abandoned, which is a division of Ser. No. 497,934, Mar. 22, 1990, abandoned.

[51] Int. Cl.$^6$ .............................. A61K 6/00; A61C 13/20
[52] U.S. Cl. ...................... 433/215; 433/216; 433/217.1; 433/226; 424/49; 514/944
[58] Field of Search .................... 424/49, 52, 53, 424/673; 252/315.01, 514; 514/900, 944; 433/215, 216, 217.1, 226

[56] References Cited

U.S. PATENT DOCUMENTS

| | | | |
|---|---|---|---|
| Re. 34,196 | 3/1993 | Munro | 433/215 |
| 767,553 | 8/1904 | Edgelow | 128/260 |
| 803,474 | 10/1905 | Dennis | 128/260 |
| 1,642,653 | 9/1927 | Goldstein | 32/5 |
| 1,691,785 | 11/1928 | Remensnyder | 260/17.4 |
| 1,934,688 | 11/1933 | Ackerman | 32/5 |
| 2,257,709 | 9/1941 | Anderson | 128/260 |
| 2,798,053 | 7/1957 | Brown | 260/2.2 |
| 2,835,628 | 5/1958 | Saffir | 167/84 |
| 2,858,281 | 10/1958 | Bauman et al. | 260/2.2 |
| 2,923,692 | 2/1960 | Ackerman et al. | 260/17.4 |
| 2,985,625 | 5/1961 | Jones | 260/78 |
| 3,057,413 | 4/1962 | Rosenthal | 424/49 |
| 3,060,935 | 10/1962 | Riddell | 128/260 |
| 3,073,300 | 1/1963 | Berghash | 128/136 |
| 3,234,942 | 2/1966 | Simor | 128/172.1 |
| 3,247,844 | 4/1966 | Berghash | 128/136 |
| 3,379,193 | 4/1968 | Monoghan | 424/49 |
| 3,380,446 | 4/1968 | Martin | 128/24 |
| 3,385,291 | 5/1968 | Martin | 128/62 |
| 3,416,527 | 12/1968 | Hoef | 128/260 |
| 3,448,738 | 6/1969 | Berghash | 128/136 |
| 3,481,329 | 12/1969 | Warren, Jr. | 128/66 |
| 3,499,844 | 3/1970 | Kibbel et al. | 252/316 |
| 3,527,218 | 9/1970 | Westine | 128/229 |
| 3,527,219 | 9/1970 | Greenberg | 128/260 |
| 3,536,069 | 10/1970 | Gores | 128/136 |
| 3,624,909 | 12/1971 | Greenberg | 32/40 |
| 3,625,215 | 12/1971 | Quisling | 128/260 |
| 3,657,413 | 4/1972 | Rosenthal | 424/81 |
| 3,742,942 | 7/1973 | Westline | 128/62 |
| 3,844,286 | 10/1974 | Cowen | 128/260 |
| 3,955,281 | 5/1976 | Weitzman | 32/14 |
| 3,969,499 | 7/1976 | Lee, Jr. et al. | 424/52 |
| 3,988,433 | 10/1976 | Benedict | 424/53 |
| 3,998,945 | 12/1976 | Vit | 424/53 |
| 4,032,627 | 6/1977 | Suchan et al. | 424/54 |
| 4,044,762 | 8/1977 | Jacobs | 128/136 |
| 4,064,628 | 12/1977 | Weitzman | 32/14 |
| 4,138,814 | 2/1979 | Weitzman | 33/14 |
| 4,164,940 | 8/1979 | Quinby | 128/62 |
| 4,173,219 | 11/1979 | Lentine | 128/260 |
| 4,173,505 | 11/1979 | Jacobs | 156/285 |
| 4,239,818 | 12/1980 | LaBate | 427/236 |
| 4,244,942 | 1/1981 | Kamishita et al. | 424/81 |
| 4,251,507 | 2/1981 | Olson | 424/49 |
| 4,302,441 | 11/1981 | Muhlemann et al. | 424/48 |
| 4,376,628 | 3/1983 | Aardse | 433/80 |
| 4,428,373 | 1/1984 | Seid et al. | 604/77 |
| 4,431,631 | 2/1984 | Clipper et al. | 424/53 |
| 4,518,721 | 5/1985 | Dhabhar et al. | 523/120 |

(List continued on next page.)

FOREIGN PATENT DOCUMENTS

| | | |
|---|---|---|
| 0 286 766 | 10/1988 | European Pat. Off. . |
| 0 325 267 | 7/1989 | European Pat. Off. . |
| 1 489 712 | 11/1965 | Germany . |
| 1 566 227 | 10/1969 | Germany . |
| 28 48 237 | 11/1978 | Germany . |
| 528007 | 12/1983 | Spain . |

OTHER PUBLICATIONS

Deposition of Dr. William Walter Klusmeier, Jr. with Exhibits. Civil Action No. 91-1406 WJR (Sx) (C.D. Cal.).
Deposition of Dan Parker with Exhibits. Civil Action No. 91-1406 WJR (Sx) (C.D. Cal.).
Declaration of Paula Rains. Civil Action No. 91-1406 WJR (Sx) (C.D. Cal.).
Declaration of Dr. Phil S. Sanders. Civil Action No. 91-1406 WJR (Sx) (C.D. Cal.).
Deposition of Dr. Phil S. Sanders with Exhibits. Civil Action No. 91-1406 WJR (Sx) (C.D. Cal.).
Declaration of Dr. Jerry Wagner. Civil Action No. 91-1406 WJR (Sx) (C.D. Cal.).
Deposition of Dr. Jerry Wagner. Civil Action No. 91-1406 WJR (Sx) (C.D. Cal.).
Deposition of Harry F. Albers with Exhibits. Civil Action No. 2:95CV 0163W (D. Utah).
Deposition of Dr. Van B. Haywood with Exhibits. Civil Action No. 2:95CV 0163W (D. Utah).
Expert Report of Dr. Van B. Haywood. Civil Action No. 2:95CV 0163W (D. Utah).

(List continued on next page.)

*Primary Examiner*—Raj Bawa

[57] ABSTRACT

The present invention discloses high viscosity sustained release dental compositions, such as tooth bleaching or fluoride compositions, for treating tooth surfaces. For maximum results, an improved dental tray having reservoirs for holding the dental composition adjacent the desired tooth surfaces is preferably used in combination with the sustained release dental composition. The sustained release dental compositions include a high carboxypolymethylene concentration which results in very high viscosity. The high level of carboxypolymethylene makes dilution of the dental compositions from saliva difficult and time consuming so that the compositions stay within the tray reservoirs, thereby providing sustained release. The concentrated carboxypolymethylene adds a unique tackiness to the dental composition which helps retain and seal the soft tray material against the patient's teeth.

24 Claims, 2 Drawing Sheets

U.S. PATENT DOCUMENTS

| | | | |
|---|---|---|---|
| 4,522,805 | 6/1985 | Gordon | 424/52 |
| 4,528,180 | 7/1985 | Schaeffer | 424/52 |
| 4,537,778 | 8/1985 | Clipper et al. | 424/53 |
| 4,560,351 | 12/1985 | Osborne | 433/80 |
| 4,568,536 | 2/1986 | Kronenthal et al. | 424/22 |
| 4,592,487 | 6/1986 | Simon et al. | 222/94 |
| 4,592,488 | 6/1986 | Simon et al. | 222/94 |
| 4,661,070 | 4/1987 | Friedman | 433/203.1 |
| 4,687,663 | 8/1987 | Schaeffer | 424/52 |
| 4,696,757 | 9/1987 | Blank et al. | 252/186.29 |
| 4,755,386 | 7/1988 | Hsiao et al. | 424/435 |
| 4,770,634 | 9/1988 | Pellico | 433/217 |
| 4,788,052 | 11/1988 | Ng et al. | 424/53 |
| 4,812,308 | 3/1989 | Winston et al. | 424/52 |
| 4,839,156 | 6/1989 | Ng et al. | 424/53 |
| 4,839,157 | 6/1989 | Ng et al. | 424/53 |
| 4,849,213 | 7/1989 | Schaeffer | 424/52 |
| 4,895,721 | 1/1990 | Drucker | 424/53 |
| 4,902,227 | 2/1990 | Smith | 433/215 |
| 4,939,284 | 7/1990 | Degenhardt | 558/142 |
| 4,954,487 | 9/1990 | Cooper et al. | 514/159 |
| 4,968,251 | 11/1990 | Darnell | 433/216 |
| 4,971,782 | 11/1990 | Rudy et al. | 424/53 |
| 4,980,152 | 12/1990 | Frazier et al. | 424/52 |
| 4,983,379 | 1/1991 | Schaeffer | 424/52 |
| 4,983,381 | 1/1991 | Zaragoza | 424/53 |
| 4,988,500 | 1/1991 | Hunter et al. | 424/53 |
| 4,990,089 | 2/1991 | Munro | 433/215 |

OTHER PUBLICATIONS

Trial Testimony of Harry F. Albers (Direct), Civil Action No. 2:95CV 0163W (D. Utah).

Trial Testimony of Dan E. Fischer (Direct and Rebuttal), Civil Action No. 2:95CV 0163W (D. Utah).

Trial Testimony of Roger Hicks (Rebuttal), Civil Action No. 2:95CV 0163W (D. Utah).

Trial Testimony of Bryan D. Tarr (Direct), Civil Action No. 2:95CV 0163W (D. Utah).

Trial Testimony of Garold S. Yost (Rebuttal), Civil Action No. 2:95CV 0163W (D. Utah).

Trial Testimony of Wayne Smith Gundry (Direct), Civil Action No. 2:95CV 0163W (D. Utah).

Trial Testimony of Walter O. Dixon (Direct), Civil Action No. 2:95CV 0163W (D. Utah).

Trial Exhibits, Civil Action No. 2:95CV 0163W (D. Utah).

"Die Wichtmetalle in der Zahntechnik." Grundwissen für Zahntechniker Werkstoffkunde, Band II, Caesar/Ernst (Erste Auflage)—Non Metals in Dental Technology, Basic Sciences for Dental Technicians, Materials Science, vol. II, 1987.

Omnii International Advertisement for White & Brite (as early as Mar. 21, 1990).

Omnii International Advertisement for Fluorides, etc. (as early as Mar. 21, 1990).

Physian's Desk Reference, 1168, 1584, published by Medical Economics Co., Inc., Oracle N., N.J., 38th Ed. 1984.

Product Insert, for Peroxgel® Oral Antiseptic & Cleanser, Lot No. 55008, Product Code Code NDC 0021–0150–12, Product Insert No. 4210220044.

Remington's Pharmaceutical Sciences, 1256, Mack Pub., 16th Ed. 1980.

Research on Whitening Teeth Makes News, *The North Carolina Dental Review* vol. 7, No. 2, p. 9, Fall 1990.

T & S Dental and Plastics Co., Inc. "Instruction Manual for the Machine Precision Vacuum Adapter," pp. 1–20 (as early as Mar. 21, 1990).

"Tooth Bleaching, Home Use Products," *Clinical Research Associates Newsletter*, vol. 13, Issue 7, pp. 1–3, Jul. 1989.

"Tooth Bleaching, Home–Use Products," *Clinical Research Associates Newsletter*, vol. 13, Issue 12, pp. 1–3, Dec. 1989.

Deposition of Dr. Thomas Marvin Austin with Exhibits, Civil Action No. 91–1406 WJR (Sx) (C.D. Cal.).

Declaration of P. Michael Clinard, Civil Action No. 91–1406 WJR (Sx) (C.D. Cal.).

Deposition (Group) of Coastal Dental Study Club, Civil Action No 91–1406 WJR (Sx) (C.D. Cal.).

Declaration of Dr. David H. Freshwater (2), Civil Action No. 91–1406 WJR (Sx) (C.D. Cal.).

Deposition of Dr. David H. Freshwater with Exhibits, Civil Action No. 91–1406 WJR (Sx) (C.D. Cal.).

Deposition of Dr. Van B. Haywood with Exhibits, Civil Action No. 91–1406 WJR (Sx) (C.D. Cal.).

Declaration of Dr. William W. Klusmeier (2), Civil Action No. 91–1406 WJR (Sx) (C.D. Cal.).

Tyldesley, W.R., "Acidic Stain Removers: A Short Report", *Dental Practitioner & Dental Record*, vol. 20, No. 9, pp. 311–313, May 1970.

Ward, Marcus L., "The American Textbook of Operative Dentistry," pp. 491–497, Lea & Febiger, 1920.

Warren, K., "Bleaching Discolored Endodontically Treated Teeth" *Restorative Dent.*, vol. 1, No. 5, Jul. 1985.

Wayman, Blake E. et al., "Vital Bleaching Technique For Treatment of Endemic Fluorosis", *General Dentistry*, pp. 424–427, Sep.–Oct. 1981.

Weisz, W.S., "Reduction of Dental Caries Through the Use of a Sodium Fluoride Mouthwash," *The Journal of the American Dental Association*, vol. 60, pp. 454–455, Apr. 1960.

Yarborough, David K., "The Safety and Efficacy of Tooth Bleaching: A Review of Literature, 1988–1990," *Compedium*, vol. 12, No. 3, pp. 191–196, Mar. 1991.

Younger, Harold B., "Bleaching Mottled Enamel", *Texas Dental Journal*, vol. 60, No. 12, pp. 467–469, Dec. 1942.

Zillich, Richard M., "Bleaching Tetracycline Stains" *The Compendium of Continuing Education*, vol. V, No. 6, p. 465–470, Jun. 1984.

"A New Look For Your Smile", *JADA Guide To Dental Health*, Special Issue, pp. 55–59, 1987.

Adept Report, "Lightening Natural Teeth," vol. 2, No. 1, pp. 1–4, Winter 1991.

BFGoodrich Chemical (Deutschland) GmbH: Carbopol$^R$, Wasserlösliche Polymere—Carbopol®, Water Soluble Polymer, 1984.

Buffalo Dental Mfg. Co. Technical Manuals for Sta–Vac mini–lab vacuum adapter, Bochure No. 895/01.

Den–Mat Corporation advertisement for "Rembrant Lighten Bleaching Gel" in *Dental Products Report*, p. 97, Feb. 1990.

*Dental Pharmacology*, pp. 296–297 (as early as Mar. 21, 1990).

*Lexikon der dentalen Technologie—Dental Technology Dictionary*, Quintessenz Verlags—GmbH, pp. 274, 275, 350, 351, 1986.

Genesis 2000 advertisement for "Genesis White" whitening system (as early as Mar. 21, 1990).

Hackh's Chemical Dictionary, p. 440, McGraw Hill, 4th Ed. 1969.

Advertisement of M & M Innovations for "Nu–Smile" dental bleaching system, which appeared in *Dental Products Report*, Nov. 1989.

Reid, J.S. "Patient Assessment of The Value of Bleaching Tetracycline–Stained Teeth", *Journal of Dentistry For Children*, pp. 353–355, Sep./Oct. 1985.

Richardson, Sue Ellen, "Home Bleaching: Effectiveness, History, Technique, Bleaches, Cost and Safety," *J. Greater Houston Dent. Soc.*, pp. 22–25, Nov. 1989.

Ripa, Louis W. et al., "Effect of Prior Toothcleaning on Biannual Professional APF Topical Fluoride Gel–tray Treatments", *Clinical Preventive Dentistry*, vol. 5, No. 4, Jul.–Aug. 1983.

Ripa, Louis W. et al., "Effect of Prior Toothcleaning on Biannual Professional Acidulated Phosphate Fluoride Topical Fluoride Gel–tray Treatments—Results After Three Years", *Caries Res.* 18: 457–464, 1984.

Seale, N.S. et al., "Systematic Assessment of Color Removal Following Vital Bleaching of Intrinsically Stained Teeth," *J. Dent. Res.*, vol. 64, No. 3, pp. 457–461, 1985.

Shapiro, William B., et al., "The Influence of Urea Peroxide Gel on Plaque, Calculus and Chronic Gingival Inflammation," *J. Periodontology*, vol. 44, No. 10, pp. 636–639, Oct. 1973.

Shipman, B., et al., "The Effect of a Urea Peroxide Gel on Plaque Deposits and Gingival Status," *J. Periodont.*, pp. 283–285, 1971.

Smith et al., "Further Studies on Methods of Removing Brown Stain from Mottled Teeth", *JADA*, vol. 29, pp. 571–576, Apr. 1942.

Spasser, Herbert F. "A Simple Bleaching Technique Using Sodium Perborate", *New York State Dental Journal*, No. 27, pp. 332–334, Aug./Sep. 1961.

Spencer, Duane E., "A Conservative Method of Treating Tetracycline Stained Teeth", *ASBC Journal of Dentistry For Children*, vol. 29, No. 6, pp. 25–28, Nov./Dec. 1972.

Stewart, George G. et al., "A Study of a New Medicament in the Chemomechanical Preparation of Inflected Root Canals," *The Journal of the American Dental Association*, vol. 63, pp. 33–37, Jul. 1961.

Stindt, Diana J. et al., "An Overview of Gly–Oxide Liquid in Control and Prevention of Dental Disease," *Compend Contin. Educ. Dent.*, vol. X, No. 9, pp. 514–519, Sep. 1989.

Swift, Edward J. Jr., "A Method For Bleaching Discolored Vital Teeth". *Quintessence International*, vol. 19, No. 9, pp. 607–612, 1988.

Tartakow et al., "Urea Peroxide Solution in the Treatment of Gingivitis in Orthodontics," *Am. J. Orthod.*, vol. 73, No. 5, pp. 560–567, May 1978.

Tassman, Gusstav et al., "Clinical Observations on Establishing Hygiene in Problem Patients," *Dental Survey*, vol. 39, pp. 35–42, Feb. 1963.

Trask, P., "Orthodontic Positioner Used for Home Fluoride Treatments", *American Journal of Orthodontics*, vol. 67, No. 6, pp. 677–682, Jun. 1975.

Lowney, Jeremiah J., "A Simplified Technique for Bleaching a Discolored Tooth," *Dental Digest*, pp. 446–448, Oct. 1964.

McEvoy, S., "Chemical Agents for Removing Intrinsic Stains from Vital Teeth. I. Technique Development", *Quintessence International*, vol. 20, No. 5, pp. 323–328, 1989.

McEvoy, S., "Chemical Agents for Removing Intrinsic Stains from Vital Teeth. II. Current Techniques and their Clinical Application", *Quintessence International*, vol. 20, No. 6, pp. 379–384, 1989.

McMurray, Crawford A., "Removal of Stains From Mottled Enamel Teeth", *Texas Dental Journal*, vol. 59, No. 9, Sep. 1941.

Mello, Hilton S., "The Mechanism of Tetracycline Staining in Primary and Permanent Teeth", *Dentistry for Children*, vol. 34, No. 6, pp. 478–487, Nov. 1967.

Merwe, P.K. v.d., "The Removal Of the Stain From Mottled Teeth", *The South African Dental Journal*, vol. 18, No. 2, pp. 31–34, Feb. 1944.

Morrison, Scott W., "Vital Tooth Bleaching—The Patient's Viewpoint", *General Dentistry*, pp. 238–240, May–Jun. 1986.

Murrin, James R., et al., "Chemical Treatment of Vital Teeth With Intrinsic Stain", *ODJ*, pp. 6–10, Nov. 1982.

Myers, Malcolm, et al., "Effect of Daily Application of Fluoride in a Custom Fitted Mouthpiece on Plaque Flora Associated with Dental Decay", *Journal of Dental Research*, vol. 50, No. 3, pp. 597–599, May 1971.

Nathanson, Dan et al., "Bleaching Vital Teeth: A Review and Clinical Study" *Compend Contin. Educ. Dent.*, vol. VIII, No. 7, pp. 490–498, Jul./Aug. 1987.

Newbrun, E., "Topical Fluoride Therapy: Discussion of Some Aspects of Toxicology, Safety, and Efficacy," *J. Dent. Res.*, vol. 66, No. 5, pp. 1084–1086, 1987.

Nutting, Edwin B., et al., "Chemical Bleaching of Discolored Endodontically Treated Teeth", *Dental Clinics of North America*, pp. 655–662, Nov., 1967.

Prinz, Herman, "Recent Improvements in Tooth Bleaching", *The Dental Cosmos*, vol. 66, pp. 558–560, May 1924.

Reddy, J. et al., "The Effect of a Urea Peroxide Rinse on Dental Plaque and Gingivitis." *J. Periodontol.*, pp. 607–610, Oct. 1976.

Rees, Terry D. et al., "Oral Ulcerations with Use of Hydrogen Peroxide," *J. Periodontol.*, pp. 689–692, 1986.

Reid, J.S. et al. "A Suggested Method of Bleaching Tetracycline–Stained Vital Teeth", *Bristish Dental Journal*, vol. 142, No. 8, p. 261, Apr. 1977.

Haywood, Van B. et al., "Nightguard Vital Bleaching", *Quintessence International*, vol. 20, No. 3, pp. 173–176, 1989.

Haywood, Van B., "Nightguard Vital Bleaching. A History and Products Update: Part 1," *Esthetic Dentistry Update*, vol. 2, No. 4, pp. 64–66, Aug. 1991.

Heller, L., "Is Your Dentist Up–To–Date?", *Redbook*, pp. 20–26, Mar. 1990.

Haywood, Van B. et al., "Nightguard Vital Bleaching: Effects on Enamel Surface Texture and Diffusion", *Quintessence International*, vol. 21, No. 10, pp. 801–804, 1990.

Haywood, Van B. "Letter to the Editor", *Quintessence International*, vol. 20, No. 10, p. 697, 1989.

Horii, A.A., et al., "A Vinyl Applicator for Assessing Drugs in the Treatment of Caries and Periodontal Disease in the Hamster," Laboratory of Histology and Pathology, National Institute of Dental Research, National Institutes of Health, Department of Health, Education, and Welfare, U.S. Public Health Service, Bethesda Maryland, p. 152 (submitted for publication Aug. 29, 1963).

Jordan, Ronald E., et al., "Conservative Vital Bleaching Treatment of Discolored Dentition", *Compendium*, vol. V, No. 10, pp. 803–808, Nov./Dec. 1984.

Jordan, Ronald E., et al., "Conservative Applications of Acid Etch–Resin Techniques", *Dental Clinics of North America*, vol. 25, No. 2, pp. 307–337, Apr. 1981.

Kaslick, Ralph S., "Studies on the Effects of a Urea Peroxide Gel on Plaque Formation and Gingivitis," *J. Periodontol*, vol. 46, pp. 230–232, No. 4, Apr. 1975.

Kehoe, Joseph C., "Bleaching Today", *Florida Dental Journal*, vol. 55, No. 1, pp. 12–15, Spring 1984.

Kennedy, Nathaniel, "The Tetracycline Dilemma and a Vital Bleaching Technique", *CDS Review*, vol. 69, No. 5, pp. 28–30, May 1976.

Kesling, Harold D., "The Tooth Positioner as the Means of Final Positioning of Teeth to a Predetermined Pattern," *Journal of Dentistry for Children*, vol. 11, 4th Quarter, pp. 103–105, 1944.

Kirkegaard et al., "Children's Response to Various Local Fluoride Treatments", *Acta Odontol. Scand.*, vol. 38, No. 4, pp. 235–240, 1980.

Kundergren et al., "In Vivo and In Vitro Studies on a New Peroxide–Containing Toothpaste", *Scand. J. Dent. Res.*, vol. 81, pp. 544–547, 1973.

LeCompte, E.J. et al., "Oral Fluoride Retention Following Various Topical Application Techniques in Children," *J. Dent. Res.*, vol. 61, No. 12, pp. 1397–1400, 1982.

Ledoux, William R., et al., "Structural Effects of Bleaching On Tetracycline–Stained Vital Rat Teeth", *The Journal of Prosthetic Dentistry*, vol. 54, No. 1, pp. 55–59, Jul. 1985.

Feiglin, Barry, "A 6–year Recall Study of Clinically Chemically Bleached Teeth," *Oral. Surg. Oral Med. Oral Pathol*, vol. 63, pp. 610–613, May 1987.

Feinman, Ronald A., "A Combination Theory" *CDA Journal*, pp. 10–13, Apr. 1987.

Feinman et al., "Chemical, Optical, and Physiologic Mechanisms of Bleaching Products: A Review," *The Bleaching Report*, vol. 3, pp. 32–37, 1991.

Feinman, Ronald A., "Matrix Vital Bleaching: A Review" *Esthetic Dentistry Update*, vol. 2, No. 3, pp. 42–47, Jun. 1991.

Feinman, Ronald A., "History of Bleaching Nonvital Teeth" *Bleaching: A New Addition to the Esthetic Dentistry Armamentarium*, pp. 11–12, 1990.

Fields, John P. "Intracoronal Bleaching of Tetracycline–Stained Teeth: A Case Report" *Journal of Endodontics*, vol. 8, No. 11, pp. 512–513, Nov. 1982.

Firestone, A.R. et al., "Effect of Topical Application of Urea Peroxide on Caries Incidence and Plaque Accumulation in Rats," *Caries Res.*, vol. 16, pp. 112–117, 1982.

Fogel, Maxwell S., et al., "Use of an Antiseptic Agent in Orthodontic Hygiene," *Dental Survey*, pp. 50–54, Oct. 1971.

Franchi, Gene J., "A Practical Technique for Bleaching Discolored Crowns of Young Permanent Incisors," *Journal of Dentistry for Children*, vol. 20, pp. 68–70, 1950.

Freedman, George A., "The Safety of Tooth Whitening," *Dentistry Today*, pp. 32–35, Apr. 1990.

Friedman et al., "Incidence of External Root Resorption and Esthetic Results in 58 Bleached Pulpless Teeth," *Endod. Dental Traumatol.*, pp. 23–26, Jun. 1987.

Gallion et al. "Vital Bleaching, Effects on Brightness", Alumni Dental Convention, Loma Linda University School of Dentistry, 1990.

Gertenrich et al., "Treatment of Dilantin Gingival Hyperplasia with Proxigel," *American Journal of Mental Deficiency*, vol. 78, No. 4, pp. 502–504, 1974.

Goldstein, Ronald E., "Bleaching Teeth: New Materials—New Role", *JADA* Special Issue, pp. 44–52, Dec. 1987.

Grogan, David Francis, "Agents Used in Bleaching Teeth", *Tufts Dental Outlook*, vol. 20, No. 1, pp. 20–23, Mar., 1946.

Hardman, Patrick K. et al., "Stability of Hydrogen Peroxide As a Bleaching Agent", *General Dentistry*, pp. 121–122, Mar./Apr. 1985.

Harrington, Gerald W. et al, "External Resorption associated with bleaching of pulpless teeth", *Journal of Endodontics*, vol. 5, No. 11, pp. 344–348, Nov. 1982.

Cohen, Steven et al. "Human Pulpal Response to Bleaching Procedures on Vital Teeth", *Journal of Endodontics*, vol. 5, No. 5, pp. 134–138, May 1979.

Colon, P.G. Jr., "Removing Fluorosis Stains From Teeth", *Quintessence International*, vol. 2, No. 6, pp. 89–93, Jun. 7, 1987.

Compton, Duane E., "Bleaching of Tetracycline–Stained Vital Teeth", *Journal of Endodontics*, vol. 5, No. 4, May 1979.

Corcoran, John F. et al., "Bleaching of Vital Tetracycline Stained Teeth", *Journal of the Michigan Dental Association*, vol. 56, No. 12, pp. 340–343, Dec. 1974.

Croll, Theodore P. et al. "Enamel Color Modification By Controlled Hydrochloric Acid–Pumice Abrasion. I. Technique and Examples"0 *Quintessence International*, vol. 17, No. 2, 1986.

Croll, Theodore P. et al. "Enamel Color Modification By Controlled Hydrochloric Acid–Pumice Abrasion. II. Further Examples" *Quintessence International*, vol. 17, No. 3, 1986.

Croll, Theodore P. et al., "A Case of Enamel Color Modification: 60 Year Results" *Quintessence International* vol. 18, No. 7, pp. 493–495, 1987.

Cvek, Miomir et al, "External Root on Resorption Following Bleaching of Pulpless Teeth With Oxygen Peroxide", *Endod. Dent. Traumatol*, vol. 1, pp. 56–60, 1985.

Darnell, Daniel H. et al., "Vital Tooth Bleaching: The White & Brite Technique," *Compend Cont. Educ. Dent.*, vol. XI, No. 2, pp. 86–94, Feb. 1990.

Davies, A.K. et al., "Photo–oxidation of Tetracycline Absorbed on Hydroxyapatite in Relation to the Light–Induced Staining of Teeth", *J. Dent. Res.*, vol. 64, No. 6, pp. 936–939, Jun. 1985.

Dickstein, Benjamin "Neonatal Oral Candidiasis: Evaluation of a New Chemotherapeutic Agent," *Clinical Pediatrics*, pp. 485–488, Aug. 1964.

Dietz, Ellen Roberta, "Bleaching Vital Teeth", *The Dental Assistant*, pp. 7–8, Jan./Feb. 1988.

Drew, Claudine Paula, "Teeth Bleaching . . . A Vital Technique For You To Know", *Dental Assisting*, pp. 23–25, Sep./Oct. 1988.

Ekstrand, Jan et al., "Systemic Fluoride Absorption Following Fluoride Gel Application," *J. Dent. Res.*, vol. 59, No. 6, p. 1067, Jun. 1980.

Englander, H.R. et al., "The Prevention of Dental Caries in the Syrian Hamster after Repeated Topical Application of Sodium Fluoride Gels" *JADA*, vol. 73, pp. 1342–1347, Dec. 1966.

Englander et al., "Clinical Anticaries Effect of Repeated Topical Sodium Fluoride Applications by Mouthpieces", *JADA*, vol. 75, pp. 638–644, Sep. 1967.

Amigoni et al., "The Use of Sodium Bicarbonate and Hydrogen Peroxide Periodontal Therapy: A Review", *JADA*, vol. 114, pp. 217–221, Feb. 1987.

Archambault, Dr. Gregory A., "Home Bleaching" *Nation–Wide Dental*, vol. 2, No. 22, Jan. 1990.

Arens, Donald E. et al., "A Practical Method of Bleaching Tetracycline–Stained Teeth", *Oral Surg., Oral Med., Oral Path*, vol. 34, No. 5, Nov. 1972.

Arzt, Alvin H. "Updating Tetracycline–Stained Teeth Bleaching Technique", *Quintessence International*, No. 1, pp. 15–18, Jan. 1981.

Attin et al., "Die Bleichbehandlung—ein fester Bestandteil ästhetischer Zahnheilkunde," Universitätsklinik für Abt. Poliklinik, Hugstetter Str. 55, 71906 Freiburg—Attin et al., Bleaching—An Essential Part of Esthetic Dentistry, University Clinic for Dentistry, Oral Medicine and Orthodontics, Polyclinic, Hugstetter Str. 55, D–79106 Freiburg, 1995.

Baumgartner, J. Craig et al., "Human Pulpal Reaction to the Modified McInnes Bleaching Technique", *Journal of Endodontics*, vol. 9, No. 12, pp. 524–529, Dec. 1983.

Bayless, J. Mark et al., "Diagnosis and Treatment of Acute Fluoride Toxicity", *JADA*, vol. 110, pp. 209–211, Feb. 1985.

Blaine, Edward et al., "Oral Hygiene Supplement for Handicapped Children," *The Journal of Dental Practice*, pp. 29–31, May 1971.

Bouschor, Charles F., "Bleaching Fluorosis Stained Teeth", *New Mexico Dental Journal*, vol. 16, No. 1, pp. 33–34, May 1965.

Bowles, William H. et al., "Pulp Chamber Penetration by Hydrogen Peroxide Following Vital Bleaching Procedures" *Journal of Endodontics*, vol. 13, No. 8, pp. 375–377, Aug. 1987.

Budaveri, S. et al., "The Merck Index," *Merck & Co., Inc.*, pp. 323, 1449 and 1450, 1989.

Budaveri, S. et al., "The Merck Index," *Merck & Co., Inc.*, pp. 1521, 1536, 1537, MISC–3 and 4, CI–337, 1989.

Christensen, Gordon J. et al., "Bleaching Vital Tetracycline Stained Teeth", *Quintessence International* vol. 9, No. 6, Jun. 1978.

Cobe, Herbert J. et al., "Urea Peroxide . . . in Glycerine", *Pennsylvania Dental Journal*, vol. 25, No. 4, pp. 12–18, Jan. 1959.

Cohen, Stephen, "A Simplified Method for Bleaching Discolored Teeth," *Digest*, pp. 301–303, Jul. 1968.

Cohen et al., "Bleaching Tetracycline–Stained Vital Teeth", *Oral Surgery*, vol. 29, No. 3, pp. 465–471, Mar. 1970.

Albers, Harry F., *Tooth Colored Restoratives: A Text for Selection, Placement, and Finishing*, 7th Ed., 1985.

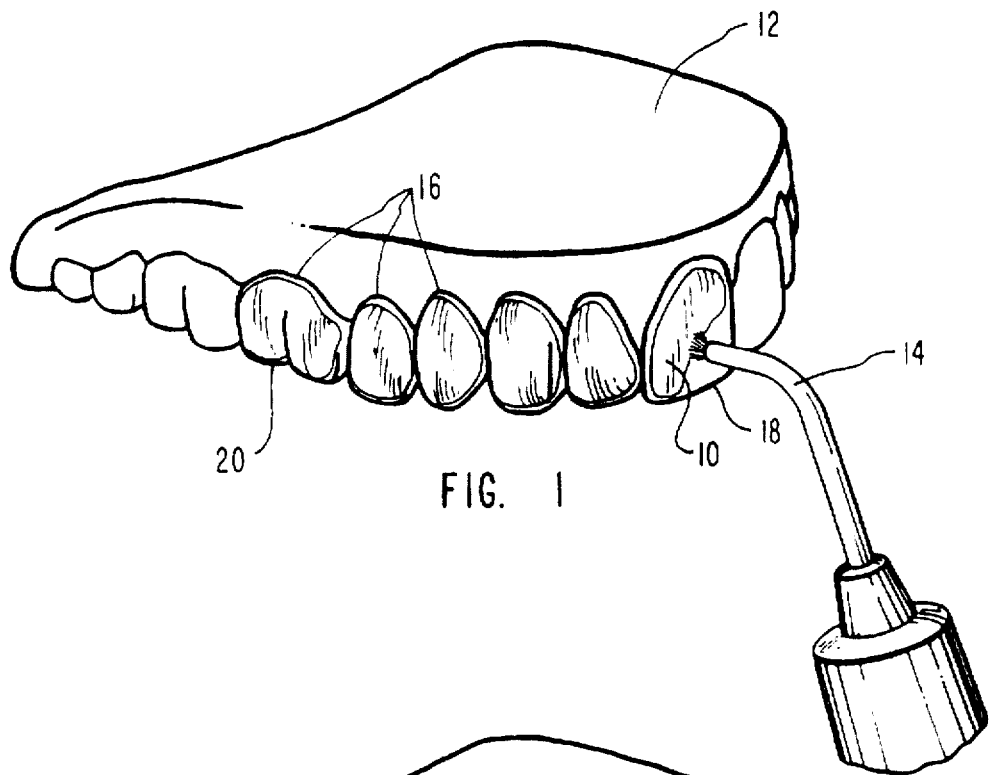
FIG. 1
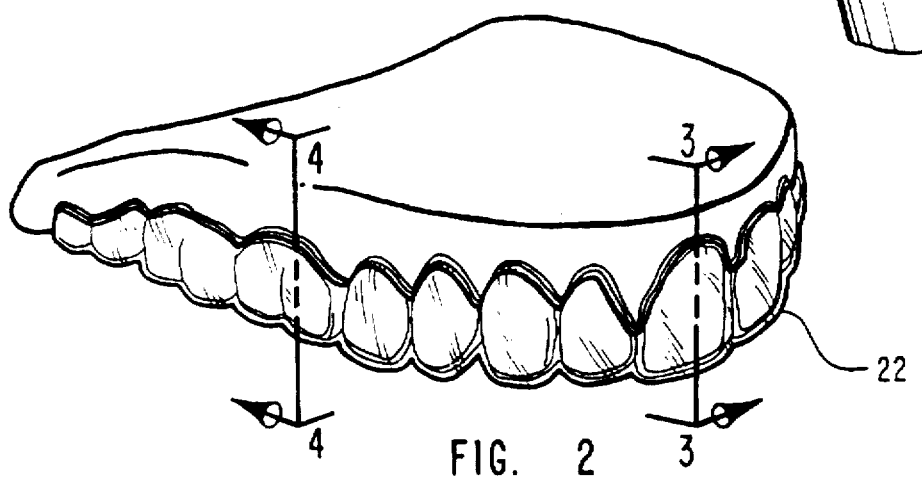
FIG. 2
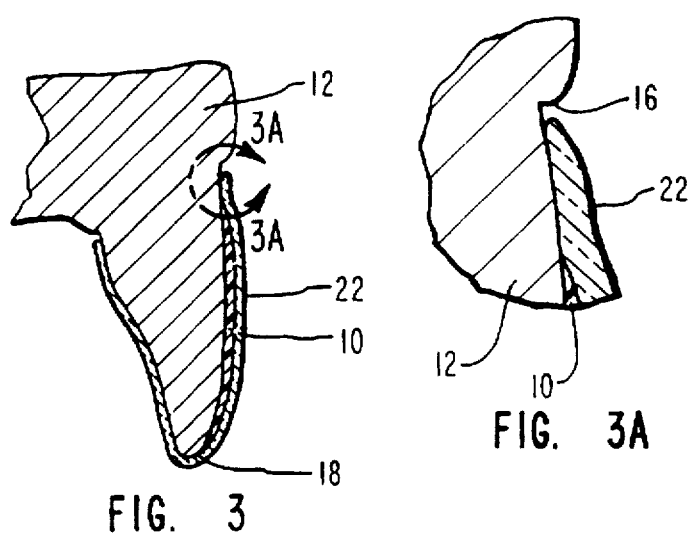
FIG. 3
FIG. 3A

METHODS FOR MANUFACTURING DENTAL TRAYS HAVING THIN WALLS FOR INCREASED COMFORT

RELATED APPLICATIONS

This application is a divisional of copending application Ser. No. 08/378,315 filed Jan. 25, 1995 in the name of Dan E. Fischer, D.D.S., for "ANTICARIOGENIC AND ANTI-MICROBIAL DENTAL COMPOSITIONS AND METHODS FOR TREATING TEETH SURFACES", which is a file wrapper continuation of application Ser. No. 08/099,247 filed Jul. 28, 1993 for "SUSTAINED RELEASE DENTAL COMPOSITIONS AND METHODS FOR TREATING TEETH SURFACES" (abandoned), which is a file wrapper continuation of application Ser. No. 07/985,700 filed Dec. 2, 1992 (abandoned), which is a file wrapper continuation of U.S. application Ser. No. 07/718,210 filed Jun. 20, 1991 (abandoned), which is a divisional of U.S. application Ser. No. 07/497,934, filed Mar. 22, 1990 (abandoned).

BACKGROUND

1. The Field of the Invention

The present invention relates to sustained release dental compositions and methods for treating teeth surfaces. More particularly, the present invention is directed to high viscosity sustained release dental compositions, such as tooth bleaching compositions, used in combination with a dental tray having reservoirs for holding the dental composition located adjacent the teeth surfaces to be treated.

2. The Relevnt Technology

Virtually all people desire white or whiter teeth. To achieve this goal, people either have veneers placed over their teeth or have their teeth chemically bleached. In the past, patients who desired to have their teeth bleached had to submit to conventional in-office bleaching techniques. This usually involved carefully placing a hydrogen peroxide solution (typically 30% $H_2O_2$) on the teeth, protecting the sensitive soft tissues with a ligated rubber dam, and applying heat or light to the solution. Such treatments typically last 30 minutes to 1 hour with from 4 to 10 appointments being necessary for a significant change. Only the labial surface of the 6–8 front teeth is treated.

Since its introduction in early 1989, there has been a growing interest among the dental profession in home-use tooth bleaching products and methods. A current representative technique includes: (1) making an alginate impression of the patient's teeth; (2) making a stone cast of the impression; (c) vacuum forming a tray from the cast, usually from thin (0.020–0.030 inch) hard transparent material, and trimming to exclude gingival coverage; (4) instructing the patient to (a) place 2–3 drops of a bleaching solution into each area of each tooth to be bleached, (b) place the tray in the mouth, (3) expectorate any excess bleaching solution, (d) change the bleaching solution every 1 to 2.5 hours, and (c) remove the tray during meals. A few recommend wearing the tray during the night.

The most commonly used dental bleaching agent is 10% carbamide peroxide ($CO(NH_2)_2H_2O_2$), also called urea hydrogen peroxide, hydrogen peroxide carbamide, and perhydrol-urea. Carbamide peroxide has been used by dental clinicians since the 1960's as an oral antiseptic. Tooth bleaching was a side effect of extended contact time. Over the counter ("OTC") compositions of 10% carbamide peroxide are available as "Gly-Oxide" by Marion Laboratories and "Proxigel" by Reed and Carnrick.

Positive results using the foregoing technique have been reported. The effectiveness depends upon such factors as type and intensity of stain, bleaching agent contact time on teeth, and amount of available active ingredient in the bleaching agent. Because the time commitment for the actual bleaching process takes place outside the dental office, the cost for the procedure is substantially less than conventional in-office bleaching techniques. Moreover, patient discomfort associated with home-use tooth bleaching techniques both during and after treatment is reportedly less than that associated with conventional in-office bleaching.

Notwithstanding the foregoing advantages, there remain some important disadvantages to home-use bleaching products and techniques. One important disadvantage is that the bleaching agent must be frequently replaced during the day. Clinical test results indicate that saliva dilution and swallowing of the bleaching agent caused the volume of agent in the tray to diminish rapidly over time, thereby decreasing the amount of active ingredient available for tooth bleaching. Test results show that after one hour, less than one-half the original volume of bleaching agent was present. Thus, existing bleaching agents should be replenished about every hour in order to be effective.

Many patient's daytime schedules do not permit them to constantly replenish the bleaching agent. In addition, even the suggestion of periodically replenishing the bleaching agent during the night would not be favorably received by most patients. Because of the inconvenience of constantly replacing the dental agent, patient compliance is difficult to maintain, and since patient compliance determines the ultimate success of the treatment, the need to constantly replace the dental bleaching agent is a major inconvenience which limits the success of the treatment.

Another disadvantage with current home-use bleaching compositions and techniques is that it often takes weeks to see an observable result. Although some have reported lightening of teeth in shorter periods of time, in most cases the home-use bleaching treatment lasts from 4 to 6 weeks. Under such circumstances, patients often lose their enthusiasm for the procedure and often stop complying with the treatment regimen.

From the foregoing, it will be appreciated that what is needed in the art are improved compositions and methods for treating tooth surfaces which facilitate patient compliance, so that the ultimate purpose of the treatment is realized.

Additionally, it would be a significant advancement in the art to provide sustained release dental compositions for treating tooth surfaces which do not need to be continuously replaced so that patient compliance is enhanced.

It would be another significant advancement in the art to provide sustained release dental compositions for treating tooth surfaces which provide a more constant level of dental agent in contact with the teeth surfaces rather than periodic high and low levels of the dental agent in contact with the patient's teeth.

It would be an additional advancement in the art to provide sustained release dental compositions and methods for bleaching a patient's teeth which provide noticeable lightening in a matter of days rather than weeks.

Such sustained release dental compositions and methods for treating tooth surfaces are disclosed and claimed herein.

BRIEF SUMMARY AND OBJECTS OF THE INVENTION

The present invention is directed to high viscosity sustained release dental compositions, such as tooth bleaching or fluoride compositions, for treating tooth surfaces. An improved dental tray having reservoirs for holding the dental composition adjacent the desired tooth surfaces is preferably used in combination with the sustained release dental composition.

One currently preferred sustained release dental composition includes a dental bleaching agent, such as carbamide peroxide. The concentration of dental bleaching agent may vary depending upon its reactivity. For carbamide peroxide, for example, the currently preferred concentration range is from about 3% to about 20%, with a range from about 4% to about 15% being most preferred.

The dental bleaching agent is preferably included in a high viscosity matrix material to form the sustained release dental composition. Suitable matrix materials are preferably safe for oral use, do not readily dissolve in saliva, and do not react with the dental bleaching agent. One currently preferred high viscosity matrix material is a supersaturated carboxypolymethylene composition. A quantity of base is preferably added to the carboxypolymethylene composition to adjust the pH to within about 5.0 to about 7.0.

The sustained release bleaching agents within the scope of the present invention have such a high viscosity that positive pressure is needed to dispense them; gravity is not sufficient. Unlike existing low-viscosity bleaching agents, the sustained release bleaching agents cannot be dispensed dropwise from a bottle. A syringe, squeezable tube, or other similar positive pressure dispensing device must be used to dispense the bleaching compositions within the scope of the present invention.

An improved dental tray having reservoirs for holding the dental composition adjacent the desired tooth surfaces is preferably used in combination with the sustained release dental composition. The general process for preparing dental trays is known in the art. For example, an alginate impression which registers all teeth surfaces plus gingival margin is made and a stone cast is promptly made of the impression. The reservoirs are prepared by building a layer of rigid material on the stone cast on specific teeth surfaces to be treated. A dental tray is then vacuum formed from the modified cast using conventional techniques. Once formed, the tray is preferably trimmed barely shy of the gingival margin on both buccal and lingual surfaces. The resulting tray provides a perfect fit of the patient's teeth with reservoirs or spaces located where the rigid material was placed on the stone cast.

The reservoirs may also be creatively built into trays to provide additional bleaching agent to specific teeth or teeth surfaces which need more whitening than others. It has also been found that patients may experience less tooth discomfort from tray pressures when using a tray with built in reservoirs.

Before commencing a home-use teeth bleaching treatment, it is recommended that the patient's teeth be clean and that there be no restorations with leaky margins or exposed dentin. If there are large areas of exposed dentin or if restorations are inadequate, patients can develop mild to moderately severe pain.

The amount of whitening obtained during tooth bleaching is dependent upon (1) the length of time each day the tray is worn; (2) the number of days the tray is worn; and (3) the susceptibility of the teeth to the bleaching agent. For maximum whitening, an accelerated treatment time of approximately 18–20 hours per day is recommended. The treatment schedule may be tailored to each patient's lifestyle or response to the treatment, but will usually include at least treatment during the patient's sleep. It has been found that treatment during sleep is the most productive single treatment time of the day since less mouth activity "pumps" material from the tray.

It is, therefore, an object of the present invention to provide improved compositions and methods for treating tooth surfaces which facilitate patient compliance, so that the ultimate purpose of the treatment is realized.

Another important object of the present invention is to provide sustained release dental compositions for treating tooth surfaces which do not need to be continuously replaced so that patient compliance is enhanced.

Yet another significant object of the present invention is to provide sustained release dental compositions for treating tooth surfaces which provide a more constant level of dental agent in contact with the teeth surfaces rather than periodic high and low levels of the dental agent in contact with the patient's teeth thereby providing noticeable lightening of a patient's teeth in a matter of days rather than weeks.

A further important object of the present invention is to provide an improved dental tray having built in reservoirs for holding dental compositions for treating tooth surfaces which enhance the effectiveness of the dental treatment and patient comfort.

These and other objects and features of the present invention will become more fully apparent from the description which follows, or may be learned by the practice of the invention.

BRIEF DESCRIPTION OF THE DRAWINGS

FIG. 1 is a perspective view of a stone cast of a patient's teeth with a rigid coating being applied to selected teeth surfaces.

FIG. 2 is a perspective view of the stone cast of FIG. 1 with a dental tray formed from the cast and trimmed according to the teachings of the present invention.

FIG. 3 is a cross-sectional view taken along line 3—3 of FIG. 2.

FIG. 3A is a close-up view of circular section 3A—3A.

DETAILED DESCRIPTION OF THE PREFERRED EMBODIMENTS

Figure 4:
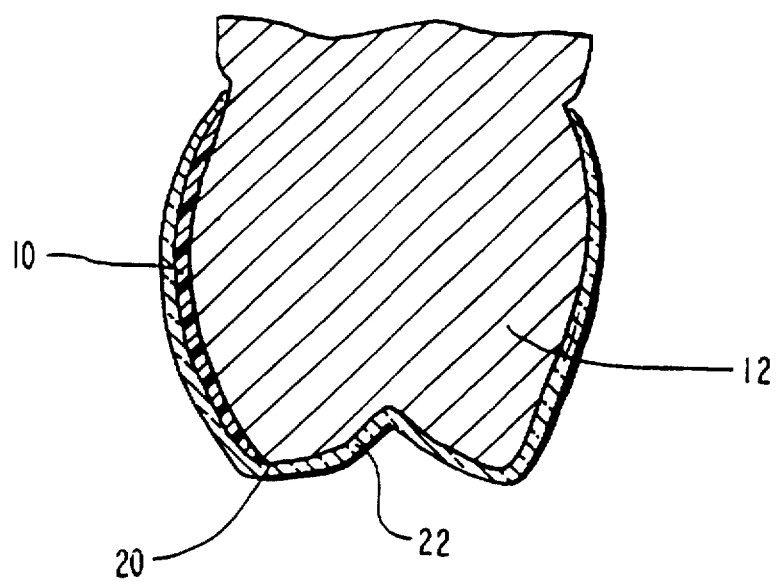
FIG. 4 is a cross-sectional view taken along line 4—4 of FIG. 2.

As summarized above, the present invention is generally related to high viscosity sustained release dental compositions, such as tooth bleaching or fluoride compositions, for treating tooth surfaces. An improved dental tray having reservoirs for holding the dental composition adjacent the desired tooth surfaces is preferably used in combination with the sustained release dental composition.

One currently preferred sustained release dental composition includes a dental bleaching agent, such as carbamide peroxide. The concentration of dental bleaching agent may vary depending upon its reactivity. For carbamide peroxide, for example, the currently preferred concentration range is from about 3% to about 20%, with a range from about 4% to about 15% being most preferred. In the case of hydrogen peroxide, which is more reactive than carbamide peroxide, the currently preferred concentration range is from about 2% to about 10%.

The dental bleaching agent is preferably included in a high viscosity matrix material to form the sustained release dental composition. Suitable matrix materials that are preferably safe for oral use, do not readily dissolve in saliva and do not react with or inactivate the dental bleaching agent. One currently preferred high viscosity matrix material is a concentrated carboxypolymethylene composition. Carboxypolymethylene is a slightly acidic vinyl polymer with active carboxyl groups. Suitable carboxypolymethylene compositions may be obtained from B. F. Goodrich Company under the tradename "carbopol".

The normal concentration of various carboxypolymethylene resins in water, according to the manufacturer, is below about 2%. However, it has been found that by preparing supersaturated carboxypolymethylene compositions having an absolute concentration in the range from about 3.5% to about 12%, preferably from 4.5% to about 10%, suitable high viscosity, sustained release dental compositions may be prepared.

Due to the large quantities of non-aqueous components in the dental compositions within the scope of the present invention, the actual concentration of carboxypolymethylene in the total quantity of water in the dental composition will preferably be in the range from about 15% to about 35%, and most preferably from about 20% to about 30%. In some special applications where very high concentrations of carboxypolymethylene are desired, the concentration of carboxypolymethylene in the total quantity of water in the dental composition may even be as great as about 40%.

One currently preferred carboxypolymethylene composition is known as Carbopol 934P. Carbopol 934P is a high purity pharmaceutical grade of Carbopol 934, having an approximate molecular weight of about 3,000,000. In addition to thickening, suspending, and emulsifying, Carbopol 934P has been used in dry tablets to impart sustained release properties. Extensive toxicity studies have been conducted on Carbopol 934P, and a master file has been established with the Food and Drug Administration. It is listed as Carbomer 934P in the National Formulary.

It is believed other carboxypolymethylene resins, such as Carbopol 940, may be substituted for the Carbopol 934P. However, based upon clinical and laboratory evaluations, it has been found that Carbopol 940 dilutes faster than Carbopol 934P. In addition, Carbopol 934P is currently preferred because it is obtainable in a pharmaceutical grade. Therefore, Carbopol 934P is a currently preferred carboxypolymethylene composition.

The concentrated carboxypolymethylene compositions within the scope of the present invention have a number of important characteristics in addition to high viscosity. Enough carboxypolymethylene is added to the dental compositions beyond that required to provide high viscosity such that a significant quantity of saliva or water is required to lower the viscosity to the point that the dental agent may be diluted and washed out by saliva. Because the high level of carboxypolymethylene makes dilution from saliva difficult and more time consuming, the resulting dental compositions provide a sustained release of the dental agent.

In most cases, high levels of carboxypolymethylene will be preferred so that the sustained release action of the dental compositions will be maintained over a greater period of time in a highly salivating patient. However, in some cases it may be desireable to use lower concentrations of carboxypolymethylene so that the sustained release action will last a shorter period of time. Thus, by varying the concentration of carboxypolymethylene, some control over the period of dental agent activity may be obtained.

The concentrated carboxypolymethylene composition also has a unique tackiness or stickiness which retains and seals the thin soft tray material against the teeth thereby preventing migration of the composition out of the tray. The tackiness of the composition also keeps the composition within the reservoirs. It has been found that if too much carboxypolymethylene is used, the tackiness decreases and the composition encumbers complete tray insertion.

In order to obtain a concentrated carboxypolymethylene composition, it is recommended that the carboxypolymethylene be mixed with a quantity of glycerine before attempting to disperse it in water. The glycerine appears to enable the large quantities of carboxypolymethylene to be dispersed in water. It has also been observed that once the carboxypolymethylene and glycerine are mixed, it is important to quickly disperse the mixture in the water or else it becomes an unmanageable solid. It is recommended that the concentration of glycerine in the final sustained release dental composition be in the range from about 20% to about 70% by weight, and preferably in the range from about 30% to about 60% by weight.

In addition to functioning as a humectant, the glycerine also provides some flavor enhancement such that a bland flavor is perceived. A few possible substitutes for glycerine include polypropylene, glycol sorbitol, some polyethylene glycols or other polyols.

It is currently preferred that the amount of water in the sustained release dental composition be in the range from about 10% to about 60% by weight, and preferably in the range from about 15% to about 40% by weight. It will be appreciated that the quantity of water in the total dental composition may come from different sources. For instance, the dental bleaching agent and base, discussed below, may come as aqueous solutions.

Because carboxypolymethylene is a polycarboxylic acid, it tends to lower the pH of the resulting bleaching composition. It appears, based upon clinical and in vitro testing, that dental compositions with a pH below about 5 are able to etch enamel. To avoid etching enamel, it is currently preferred to have the pH of the sustained release bleaching composition in the range from about 5 to about 7. This is most easily accomplished by adding a base to the composition to adjust the pH. Inorganic and organic bases may be used, with the use of concentrated sodium hydroxide (50% NaOH) being one currently preferred embodiment. Although it is possible to use lower concentrations of sodium hydroxide or other bases, such as triethanolamine, there is a risk that the lower concentrations may dilute the dental composition and affect its viscosity or sustained release characteristics.

An important characteristic of the high viscosity, sustained release dental compositions within the scope of the present invention is that the compositions are still observed, from a clinical standpoint, after about 3 to 7 hours of normal daytime activity and after about 7 to 10 hours of sleep. That is, the sticky, high viscosity dental composition is still observable in the dental tray after an extended period of time, such as at the end of the night.

Unlike existing low-viscosity bleaching agents which are placed drop-by-drop into the tray, the sustained release bleaching agents within the scope of the present invention have such a high viscosity that they cannot be dispensed drop-wise into the tray from a bottle. Positive pressure is needed to expel the sustained release bleaching agents of the present invention; gravity is not sufficient.

One currently preferred method of dispensing the bleaching agent uses a syringe. Squeezable tubes and other similar dispensing devices may also be used to dispense the bleaching agent. Upon dispensing, the sustained release bleaching agent is sufficiently viscous that it does not settle or spread when dispensed, but remains as a single extruded strand of bleaching agent.

It is currently preferred to provide a unit dose of the dental agent in a syringe or similar dispensing device. In this way, the patient can load the precise amount of dental agent onto the dental tray for each treatment period. By using such dispensing devices, the dentist is also able to monitor how many doses the patient has received and used.

An improved dental tray having reservoirs for holding the dental composition adjacent the desired tooth surfaces is preferably used in combination with the sustained release dental composition. The general process for preparing dental trays is known in the art. For example, an alginate impression which registers all teeth surfaces plus gingival margin is made and a stone cast is promptly made of the impression. Excess stone is trimmed away for ease of manipulation and forming of the plastic tray.

Reference is now made to FIGS. 1-4. The present invention modifies known procedure by applying a thin coating 10 of rigid material to stone cast 12 over the teeth surfaces to be treated. As shown in FIG. 1, coating 10 may be conveniently applied using a brush tipped applicator 14. The coating may be also light cured for convenience. Care is taken to ensure that coating 10 is kept a distance greater than about 1 mm from gingival line 16 and preferably kept from about 1¼ mm to about 1½ mm from gingival line or margin 16. The finished coating is preferably about ½ mm thick. It is particularly important when applying the rigid coating material to not cover over incisal edges 18 and occlusal edges 20. These edges should contact the finished tray to prevent vertical movement of the tray during use which could act as a pump by expressing out the bleaching agent and sucking in saliva.

A dental tray 22 is then vacuum formed from the modified cast using conventional techniques. Tray 22 is preferably constructed of soft transparent vinyl material having a preformed thickness from about 0.04 inch to about 0.06 inch. Soft material is more comfortable for the patient to wear. Most patients will find 0.04 inch to be suitable. It will be appreciated that the final tray thickness may vary depending on the technique used to prepare the tray. Patients suspected of being bruxers or hard biters may require either a thicker or a harder material. Of course, patients should be counselled to not eat with trays in place or to bite firmly into them. In extreme cases, a thicker or harder plastic may be necessary.

Once formed, tray 22 is preferably trimmed barely shy of gingival margin 16 on both buccal and lingual surfaces. Enough tray material should be left to assure that all of the tooth will be covered to within about ¼ mm to about ⅓ mm of the gingival border upon finishing and beveling of the tray periphery. It is also important to scallop up and around interdental papilla so that the finished tray does not cover them. All tray edges are preferably smoothed so that the lip and tongue will not feel an edge prominence. Slight adjustments to the tray may be made by carefully heating and stretching the tray material.

From practice, it has been found that patients may experience less tooth discomfort from tray pressures when using a tray with reservoirs built into the tray as described above. It is currently believed this is due to the fact that the teeth are not held as firmly by the tray, so "orthodontic" pressures experienced by teeth from tray indiscrepancies are minimized. The use of thin, soft tray materials further minimizes these "orthodontic" forces, compared to the harder plastics currently used in the art.

Reservoirs may also be creatively built into trays to provide additional bleaching agent to one or more teeth of an arch needing more whitening than others or to selected parts of a tooth needing more whitening than other parts.

To achieve most rapid results, it is recommended to use sustained release bleaching agents within the scope of the present invention in combination with the trays incorporating reservoirs. Nevertheless, it has been observed that bleaching occurs much more rapidly using conventional trays with sustained release bleaching compositions of the present invention than with existing bleaching agents. In addition, some increase in effectiveness has also been observed when using existing bleaching agents with trays incorporating reservoirs compared to conventional trays without reservoirs.

Before commencing a home-use teeth bleaching treatment, it is recommended that the patient's teeth be clean of calculus and external stains. Restorations should be water tight and all dentin, particularly gingival dentin with potential or existing sensitivities, should be covered. It has been observed that exposed root surfaces may experience sensitivity from sustained release bleaching agent within the scope of the present invention. In many cases dentin may be covered with a layer of dentin bonding agent or sealant to prevent this.

Since most patients will want to complete their treatment as soon as possible, recommended treatment times start at approximately 18-20 hours a day. Patients are instructed to insert the tray loaded with fresh bleaching agent after each meal and before going to bed for most rapid results. Gum soreness or other patient discomfort has been reported more often for such accelerated treatment schedules that go longer than one to two days.

A second possible treatment schedule is to allow a break-time to occur between dinner and bed. This allows the patient to participate in evening social functions without wearing the tray. In addition, oral tissues are allowed to rest during the break-time.

Another recommended treatment schedule, particularly for those where the treatment may require more than one or two days, is to load and insert the tray only before bed and after lunch. This gives the teeth and soft tissues a rest for approximately two 4-5 hour intervals between the two longer treatment periods. Potential soreness is most often prevented this way and treatment time may only be extended 20% to 30% over the more accelerated treatment schedules.

Finally, for those patients who are often in public or those who have experienced moderate or greater problems of soreness, it is recommended that the tray be worn only at night. During sleep is the most productive single treatment time since less mouth activity "pumps" material from the tray.

Regardless of which treatment schedule is used, the use of sustained release dental bleaching compositions within the scope of the present invention provides a more constant level of bleaching agent adjacent the teeth than existing home-use bleaching systems. Even if patient compliance with existing home-use dental bleaching systems is such that fresh bleaching agent is added every hour, there still would be periodic high and low levels of bleaching agent adjacent the teeth. Since the amount and length of time the active bleaching agent is adjacent the teeth significantly influences the efficiency of the treatment, the sustained release bleaching compositions and methods of the present invention represent a significant improvement over existing home-use dental bleaching systems.

At the end of the bleaching treatment, a sustained release fluoride composition may optionally be administered to the patient. For convenience, the same tray may be used to treat the teeth with fluoride as was used to bleach the teeth. Such fluoride treatment regimens may include 3 or 4 two hour treatments over 1-2 days.

The following examples set forth various sustained release dental compositions within the scope of the present invention. These examples are intended to be purely exemplary and should not be viewed as limiting the scope of the present invention.

EXAMPLE 1

A sustained release dental bleaching composition within the scope of the present invention was prepared by combining the following ingredients:

| Ingredient | | |
|---|---|---|
| Carbamide peroxide | 13.2 gm | 10% |
| Water | 27.5 gm | 21% |
| Glycerine | 74.6 gm | 57% |
| Carbopol 934P | 9.5 gm | 7% |
| Sodium hydroxide (50%) | 6.5 gm | 5% |

The Carbopol 934P was obtained from B. F. Goodrich Company, Cleveland, Ohio. The carbopol was combined with the glycerine and then quickly mixed with the water. The glycerine enables the carbopol to be dispersed in the water. The carbamide peroxide was dissolved in the water before the glycerine-carbopol mixture was added to the water. The foregoing composition had a percentage of carbopol in water of about 25.7%. The sodium hydroxide was gradually blended into the homogeneous composition in order to raise the pH to an acceptable level.

The foregoing procedure produced in a sustained release dental bleaching composition which was placed in a dental tray such as that described in connection with FIGS. 1–4 and worn by a patient for 9 hours. Subsequent examination of the patient's teeth indicated that the teeth had whitened 1–1.5 units on a Vita shade guide and that significant quantities of the sustained release bleaching composition was still observed in the application tray.

EXAMPLE 2

A sustained release dental bleaching composition within the scope of the present invention is made according to the procedure of Example 1, except that the ingredients are combined in the following amounts:

| Ingredient | Weight Percent |
|---|---|
| Carbamide peroxide | 20 |
| Water | 20 |
| Glycerine | 40 |
| Carbopol 934P | 12 |
| Sodium hydroxide | 8 |

The foregoing procedure results in a sustained release dental bleaching composition. The foregoing composition has a percentage of carbopol in water of about 37.5%. The composition possesses a high viscosity and excellent sustained release teeth bleaching activity.

EXAMPLE 3

A sustained release dental bleaching composition within the scope of the present invention is made according to the procedure of Example 1, except that the ingredients are combined in the following amounts:

| Ingredient | Weight Percent |
|---|---|
| Carbamide peroxide | 5 |
| Water | 20 |
| Glycerine | 60 |
| Carbopol 934P | 10 |
| Sodium hydroxide | 5 |

The foregoing procedure results in a sustained release dental bleaching composition. The foregoing composition has a percentage of carbopol in water of about 33.3%. The composition possesses a high viscosity and excellent sustained release teeth bleaching activity.

EXAMPLE 4

A sustained release dental bleaching composition within the scope of the present invention is made according to the procedure of Example 1, except that the ingredients are combined in the following amounts:

| Ingredient | Weight Percent |
|---|---|
| Carbamide peroxide | 10 |
| Water | 40 |
| Glycerine | 30 |
| Carbopol 934P | 12 |
| Sodium hydroxide | 8 |

The foregoing procedure results in a sustained release dental bleaching composition. The foregoing composition has a percentage of carbopol in water of about 23.1%. The composition possesses a high viscosity and excellent sustained release teeth bleaching activity.

EXAMPLE 5

A sustained release dental bleaching composition within the scope of the present invention is made according to the procedure of Example 1, except that the ingredients are combined in the following amounts:

| Ingredient | Weight Percent |
|---|---|
| Carbamide peroxide | 18 |
| Water | 15 |
| Glycerine | 60 |
| Carbopol 934P | 4 |
| Sodium hydroxide | 3 |

The foregoing procedure results in a sustained release dental bleaching composition. The foregoing composition has a percentage of carbopol in water of about 21.1%. The composition possesses a high viscosity and excellent sustained release teeth bleaching activity.

EXAMPLE 6

A sustained release dental bleaching composition within the scope of the present invention is made according to the procedure of Example 1, except that the ingredients are combined in the following amounts:

| Ingredient | Weight Percent |
| --- | --- |
| Carbamide peroxide | 14 |
| Water | 10 |
| Glycerine | 70 |
| Carbopol 934P | 3.5 |
| Sodium hydroxide | 2.5 |

The foregoing procedure results in a sustained release dental bleaching composition. The foregoing composition has a percentage of carbopol in water of about 25.9%. The composition possesses a high viscosity and excellent sustained release teeth bleaching activity.

EXAMPLE 7

A sustained release dental bleaching composition within the scope of the present invention is made according to the procedure of Example 1, except that the ingredients are combined in the following amounts:

| Ingredient | Weight Percent |
| --- | --- |
| Carbamide peroxide | 5 |
| Water | 60 |
| Glycerine | 20 |
| Carbopol 934P | 10 |
| Sodium hydroxide | 5 |

The foregoing procedure results in a sustained release dental bleaching composition. The foregoing composition has a percentage of carbopol in water of about 14.3%. The composition possesses a high viscosity and excellent sustained release teeth bleaching activity.

EXAMPLE 8

A sustained release dental fluoride composition within the scope of the present invention was prepared by combining the following ingredients:

| Ingredient | Weight | Weight Percent |
| --- | --- | --- |
| Sodium fluoride | 52 gm | 1.1% |
| Water | 1000 gm | 21.5% |
| Glycerine | 2980 gm | 64.1% |
| Carbopol 934P | 380 gm | 8.2% |
| Sodium hydroxide (50%) | 238 gm | 5.1% |

The foregoing ingredients are mixed according to the procedure of Example 1, except that sodium fluoride is used instead of carbamide peroxide. The fluoride concentration is preferably maintained at about 1.1% so that the free fluoride ion concentration is about 0.5%. The foregoing composition has a percentage of carbopol in water of about 27.5%. The foregoing procedure produces a sustained release dental fluoride composition suitable for use with a dental tray such as that described in connection with FIGS. 1–4.

Although the foregoing discussion has focused on sustained release dental bleaching or fluoride compositions, it will be appreciated that other sustained release dental compositions may also be prepared and used within the scope of the present invention. For instance, anticariogenic agents such as chlorhexidine gluconate and antimicrobial agents for treating periodontal pockets such as tetracycline may be incorporated into sustained release compositions. When the sustained release dental compositions are for treating soft tissues, the preferred tray design may need to be altered so that the tray overlaps the patient's gums.

In some cases, the sustained release dental agents may be used without a dental tray. For example, a sustained release dental composition having an antimicrobial agent may be expressed directly into periodontal pockets. In such compositions, it would be preferred to maximize the carboxypolymethylene concentration so that the effects of saliva dilution are minimized. In addition, mucosal adhesive materials may be added to the composition to further assist in retaining the composition within the periodontal pocket. Sustained release action may last from hours to days, depending on the patient's oral and salival activity.

From the foregoing, it will be appreciated that the present invention provides improved compositions and methods for treating tooth surfaces which facilitate patient compliance, so that the ultimate purpose of the treatment is realized.

Additionally, it will be appreciated that the present invention further provides sustained release dental compositions for treating tooth surfaces which do not need to be continuously replaced so that patient compliance is enhanced. The present invention also provides sustained release dental compositions for treating tooth surfaces which permit a more constant level of the dental agent to be in contact with the teeth surfaces rather than periodic high and low levels of the dental agent in contact with the patient's teeth.

It will be further appreciated that the present invention provides sustained release dental compositions and methods for bleaching a patient's teeth which provide noticeable lightening in a matter of days rather than weeks.

In addition, it will be appreciated that the present invention provides an improved dental tray having built in reservoirs for holding dental compositions for treating tooth surfaces which enhance the effectiveness of the dental treatment and patient comfort.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A method for preparing a dental tray incorporating one or more reservoirs therein for use in applying a dental composition to a person's teeth, the method comprising the steps of:

(a) obtaining an impression of at least a portion of the person's teeth and gingival margin;

(b) preparing a stone cast from the impression, the stone cast including a portion representative of the person's teeth and a portion representative of the person's gingival margin;

(c) coating at least a part of the portion of the stone cast representative of the person's teeth with a flowable coating composition which forms a hardened coating on the stone cast, the coating composition being place to correspond to one or more reservoirs that will be formed within the dental tray for holding a quantity of the dental composition;

(d) forming the dental tray from the stone cast using a preformed polymeric sheet, the hardened coating composition on the stone cast resulting in the one or more reservoirs being formed within the dental tray; and (e) trimming the dental tray to keep the dental tray from extending onto the portion representative of the gingival margin.

2. A method for preparing a dental tray as defined in claim 1, wherein the polymeric sheet comprise a soft vinyl polymer.

3. A method for preparing a dental tray as defined in claim 1, wherein the polymeric sheet comprises a sheet having a preformed thickness in a range from about 0.04 inch to about 0.06 inch.

4. A method for preparing a dental tray as defined in claim 1, wherein the impression of the person's teeth is made using an alginate composition.

5. A method for preparing a dental tray as defined in claim 1, wherein the stone cast representative of the person's teeth is made using plaster of paris.

6. A method for preparing a dental tray as defined in claim 1, wherein the coating composition is applied using a brush tip applicator.

7. A method for preparing a dental tray as defined in claim 1, wherein the stone cast is coated to keep the coating composition from covering the portion of the stone cast representative of the person's gingival margin person's.

8. A method for preparing a dental tray as defined in claim 7, wherein the coating composition is kept a distance greater than about 1 mm from the portion of the stone cast representative of the person's gingival margin.

9. A method for preparing a dental tray as defined in claim 7, wherein the coating composition is kept a distance in a range from about 1¼ mm to about 1½ mm from the portion of the stone cast representative of the person's gingival margin.

10. A method for preparing a dental tray as defined in claim 1, wherein the stone cast is coated to keep the coating composition from covering the portion of the stone cast representative of incisal edges and occlusal edges of the person's teeth.

11. A method for preparing a dental tray as defined in claim 1, wherein the coating composition becomes rigid on the stone cast.

12. A method for preparing a dental tray as defined in claim 1, wherein the coating composition has a thickness of about ½ mm upon hardening.

13. A method for preparing a dental tray as defined in claim 1, wherein the coating composition is light cured.

14. A method for preparing a dental tray as defined in claim 1, wherein the dental tray is formed by vacuum forming the polymeric sheet.

15. A method for preparing a dental tray as defined in claim 1, wherein the dental tray is formed from a soft polymeric sheet.

16. A method for preparing a dental tray as defined in claim 1, wherein the dental tray is formed from a more rigid polymeric sheet.

17. A method for preparing a dental tray as defined in claim 1, wherein the dental tray is trimmed such that the dental tray is kept a distance greater than about ¼ mm from the gingival margin represented on the stone cast.

18. A method for preparing a dental tray as defined in claim 1, further including the step of scalloping the dental tray to have an upper rim that is scalloped up and around interdental papilla represented on the stone cast.

19. A method for preparing a dental tray as defined in claim 1, further including the step of smoothing the tray edges.

20. A method for preparing a dental tray as defined in claim 1, further including the step of adjusting the dental tray by heating and then stretching the dental tray.

21. A method for preparing a dental tray as defined in claim 1, wherein the tray is prepared in a manner such that it exerts no significant orthodontic pressure upon being placed over the person's teeth.

22. A method for preparing a dental tray incorporating one or more reservoirs therein for use in applying a dental composition to a person's teeth, the method comprising the steps of:

(a) obtaining an impression of at least a portion of the person's teeth and gingival margin;

(b) preparing a stone cast of the person's teeth from the impression, the stone cast including a portion representative of the person's teeth and a portion representative of the person's gingival margin;

(c) applying a light-curable resin to at least a part of the portion of the stone cast representative of the person's teeth, the light-curable resin being applied to correspond to one or more reservoirs that will be formed within the dental tray for holding a quantity of the dental composition;

(d) exposing the light-curable resin to light in order to harden the light-curable resin;

(e) vacuum forming the dental tray from the stone cast using a preformed polymeric sheet, the hardened light-curable resin on the stone cast resulting in the one or more reservoirs being formed within the dental tray; and (e) trimming the dental tray to keep the dental tray a distance greater than about ¼ mm from the gingival margin represented on the stone cast.

23. A method for preparing a dental tray as defined in claim 22, further including the step of scalloping the dental tray to have an upper rim that is scalloped up and around interdental papilla of the person's teeth.

24. A method for preparing a dental tray incorporating one or more reservoirs therein for use in applying a dental composition to a person's teeth, the method comprising the steps of:

(a) obtaining an alginate impression of at least a portion of the person's teeth, gingival margin, and interdental papilla;

(b) preparing a stone cast of the person's teeth from the alginate impression, the stone cast including a portion representative of the person's teeth, a portion representative of the person's gingival margin, and a portion representative of the person's interdental papilla;

(c) applying a light-curable resin to at least a part of the portion of the stone cast representative of the person's teeth, the light-curable resin being applied to correspond to one or more reservoirs that will be formed within the dental tray for holding increased quantities of the dental composition against the person's teeth, the light-curable resin being kept a distance greater than about 1 mm from the gingival margin represented on the stone cast;

(d) exposing the light-curable resin to light in order to harden the light-curable resin;

(e) vacuum forming the dental tray from the stone cast using a thin, flexible preformed polymeric sheet, the dental tray having one or more reservoirs corresponding to where the light-curable resin was applied to the stone cast;

(e) trimming the dental tray to keep the dental tray a distance greater than about ¼ mm from the gingival margin represented on the stone cast; and (f) scalloping the dental tray to have a periphery that is scalloped up and around the person's interdental papilla represented on the stone cast.

* * * * *

UNITED STATES PATENT AND TRADEMARK OFFICE
CERTIFICATE OF CORRECTION

PATENT NO. : 5,759,037            Page 1 of 2
DATED       : June 2, 1998
INVENTOR(S) : Dan E. Fischer It is certified that error appears in the above-identified patent and that said Letters Patent is hereby corrected as shown below:

On the title page,:

Add the following item [73]        --Assignee: Ultradent Products, Inc., South Jordan, Utah--

Under - Attorney, Agent or Firm is missing.     --Workman, Nydegger & Seeley--

Col. 1, line 32, delete "Relevnt" and replace with --Relevant--

Col. 1, line 50, delete "(c)" and replace with --(3)--

Col. 1, line 55, delete "(3)" and replace with --(c)--

Col. 1, line 56, delete "(c)" and replace with --(e)--

Col. 5, line 1, after "use" delete ","

UNITED STATES PATENT AND TRADEMARK OFFICE
CERTIFICATE OF CORRECTION

PATENT NO. : 5,759,037
DATED : June 2, 1998
INVENTOR(S) : Dan E. Fischer

It is certified that error appears in the above-identified patent and that said Letters Patent is hereby corrected as shown below:

Col. 6, line 23, after "polypropylene" delete "," and after "glycol" add --,-

Col. 12, line 57, delete "place" and replace with --placed--

Col. 13, line 2, delete "comprise" and replace with --comprises--

Col. 13, line 18, delete the second reference to "person's"

Col. 14, line 22, delete "(e)" and replace with --(f)--

Col. 14, line 59, delete "(e)" and replace with --(f)--

Col. 14, line 63, delete "(f)" and replace with --(g)--

Signed and Sealed this

Twenty-second Day of June, 1999

Attest:

Q. TODD DICKINSON

*Attesting Officer*     *Acting Commissioner of Patents and Trademarks*